(12) United States Patent
Döring et al.

(10) Patent No.: US 7,705,991 B2
(45) Date of Patent: Apr. 27, 2010

(54) GAS CONCENTRATION MEASURING APPARATUS

(75) Inventors: Ralf Döring, Lubeck (DE); Andreas Gerk, Bad Schwartau (DE); Günter Steinert, Bad Oldesloe (DE); Peter Drever, Pansdorf (DE)

(73) Assignee: Draeger Medical AG & Co. KG, Luebeck (DE)

( * ) Notice: Subject to any disclaimer, the term of this patent is extended or adjusted under 35 U.S.C. 154(b) by 147 days.

(21) Appl. No.: 11/902,537

(22) Filed: Sep. 24, 2007

(65) Prior Publication Data

US 2008/0074647 A1    Mar. 27, 2008

(30) Foreign Application Priority Data

Sep. 26, 2006    (DE) .................. 10 2006 045 253

(51) Int. Cl.
*G01J 3/45* (2006.01)
*G01B 11/02* (2006.01)
*G01B 9/02* (2006.01)

(52) U.S. Cl. ...................... 356/454; 356/519

(58) Field of Classification Search ................. 356/454, 356/480, 481, 519, 517
See application file for complete search history.

(56) References Cited

U.S. PATENT DOCUMENTS

| 5,040,895 | A | | 8/1991 | Laurent et al. |
| 5,218,422 | A | * | 6/1993 | Zoechbauer ................ 356/454 |
| 5,561,523 | A | | 10/1996 | Blomberg et al. |
| 5,835,216 | A | | 11/1998 | Koskinen |
| 5,886,247 | A | * | 3/1999 | Rabbett ...................... 73/23.2 |

FOREIGN PATENT DOCUMENTS

DE    196 28 310    4/1997

* cited by examiner

*Primary Examiner*—Patrick J Connolly
(74) *Attorney, Agent, or Firm*—Walter Ottesen

(57) ABSTRACT

A gas concentration measuring apparatus is in miniaturized form and permits the measurement of anesthetic gas components. A variable interferometer is provided on the basis of a Fabry Perot interferometer (1) wherein the mirrors (2, 3) can be changed in spacing with respect to each other. The mirrors (2, 3) have coatings which make possible the transmission in two spectral ranges ($\Delta\lambda_1$, $\Delta\lambda_2$).

6 Claims, 3 Drawing Sheets

GAS CONCENTRATION MEASURING APPARATUS

CROSS REFERENCE TO RELATED APPLICATION

This application claims priority of German patent application no. 10 2006 045 253.4, filed Sep. 26, 2006, the entire content of which is incorporated herein by reference.

FIELD OF THE INVENTION

The invention relates to a gas concentration measuring apparatus for determining the component of inhalation anesthetics, carbon dioxide and nitrous oxide in a gas sample.

BACKGROUND OF THE INVENTION

Infrared optical systems having optical interference filters are often utilized for gas concentration measurements of anesthesia gases such as inhalation anesthetics, carbon dioxide and nitrous oxide. German Patent 196 28 310 C2 discloses a gas analyzer comprising a radiation source, a measuring path accommodating the gas sample and a detector which is connected to an evaluation unit. With the aid of the rotating filter wheel, different interference filters are sequentially introduced into the beam path and the wavelengths of these filters are matched to the absorption wavelengths of the gas components to be detected. For measuring inhalation anesthetics, the transmission wavelengths of the filters lie in a range between 8 micrometers and 12 micrometers; whereas, for nitrous oxide and carbon dioxide, the transmission wavelengths lie in the range between 3.5 micrometers and 4.5 micrometers. Eight interference filters are mounted on the filter wheel in the known gas analyzer. Furthermore, an evaluation method is provided for identifying inhalation anesthetics.

Drift effects can be compensated with reasonable complexity because the gas concentration measurement is carried out with only a radiation source and a detector. However, the measurement method with the use of movable parts is very cost intensive and subjected to wear. A measurement system of this kind cannot be miniaturized because of the number of interference filters to be accommodated on the filter wheel. Since the interference filters are always assigned to specific transmission wavelengths of the gas components to be detected, additional hydrocarbons such as alcohol or methane, which also can be contained in the breathing gas, cannot be detected without additional interference filters. These hydrocarbons affect the gas concentration measurements of the remaining anesthesia gas constituents.

A variable interferometer arrangement on the basis of a Fabry Perot interferometer affords certain advantages compared to an infrared absorption measurement with the wavelengths fixed by interference filters. A Fabry Perot interferometer of this kind comprises two partially transmissive mirrors which are aligned parallel with respect to each other and whose spacing to each other is changed. With the change of the mirror spacing, the possibility is afforded to evaluate a defined spectral range. Such interferometers can be manufactured cost effectively in miniaturized form because of silicon thin film technology. An interferometer of the above kind is described in U.S. Pat. No. 5,561,523 which is incorporated herein by reference. However, the wavelength range, which is to be evaluated for the gas concentration measurement of anesthesia gases, cannot be covered with the known interferometer.

SUMMARY OF THE INVENTION

It is an object of the invention to provide a gas concentration measuring apparatus of miniaturized construction with which the measurement of anesthesia gases is possible.

The gas measuring apparatus of the invention is for measuring a gas sample of inhalation anesthetics, carbon dioxide and nitrous oxide. The apparatus includes: radiation source means for emitting radiation in first and second spectral ranges ($\Delta\lambda_1$, $\Delta\lambda_2$); a measuring gas cuvette for accommodating the gas sample to be examined; a mirror assembly including: first and second reflecting mirrors disposed at a distance from each other; and, means for changing the distance between the mirrors; the mirror assembly being configured on the basis of an electrically tunable Fabry Perot interferometer which provides transmissions corresponding to the first and second spectral ranges ($\Delta\lambda_1$, $\Delta\lambda_2$); a detector element for evaluating the first and second spectral ranges ($\Delta\lambda_1$, $\Delta\lambda_2$); and, a drive unit connected to the mirror assembly for presetting a dynamic range with a frequency $f_2$ for changing the distance so as to permit a first spectral range ($\Delta\lambda_1$) to be detected in a transmission range of between approximately 3.5 micrometers and 4.5 micrometers and a second spectral range ($\Delta\lambda_2$) to be detected in a transmission range of between approximately 8 micrometers and 12 micrometers.

The advantage of the invention is essentially that the mirrors of a Fabry Perot interferometer are vapor deposited in such a manner that transmissions in two spectral ranges are possible. The spectral ranges are assigned to the anesthesia gas components to be detected. The spectral ranges correspond to the transmissions of the first order and of the second order of the spectrum. The spacing of the mirrors of the Fabry Perot interferometer is so changed that both spectral ranges are detected and both spectral ranges are simultaneously evaluated with a detector element.

In an advantageous manner, the radiation source comprises a first radiation source, which can be rapidly modulated and is driven up to a first emission range below a wavelength of 6 micrometers, and a broadband radiator as a second radiation source for the range between 8 micrometers and 12 micrometers.

In an advantageous embodiment, a single radiation source comprises a radiator, which can, for example, be a radiator capable to be modulated, in the form of a tungsten filament with a quartz glass envelope set thereupon as a broadband radiator.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
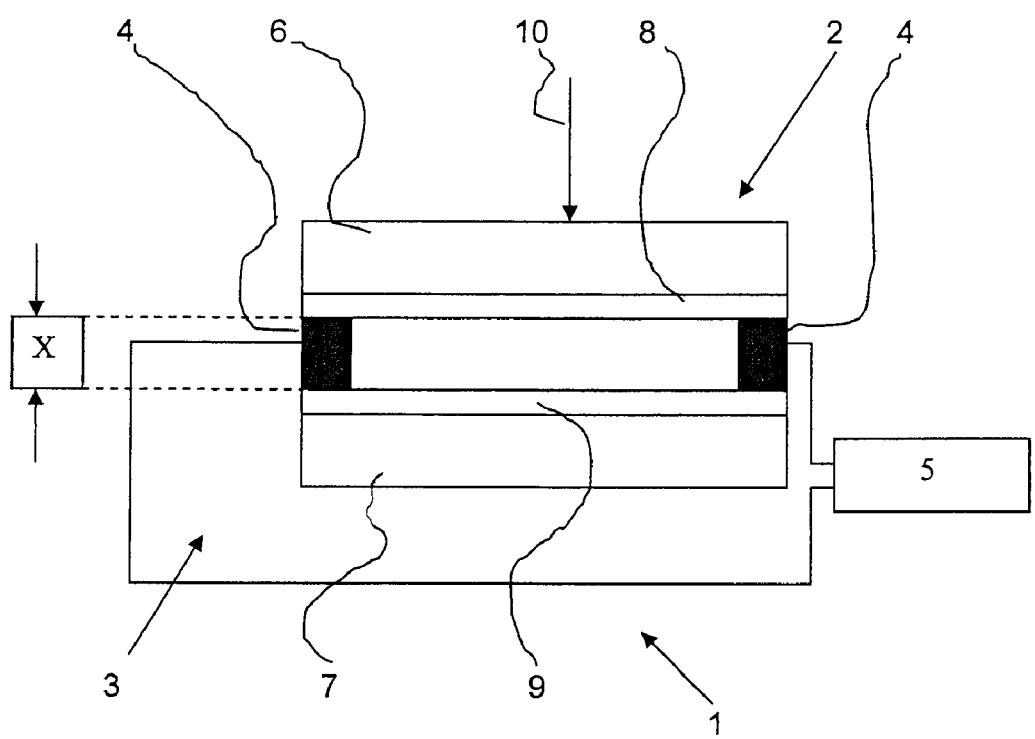
FIG. 1 is a schematic showing the configuration of a double band Fabry Perot interferometer.

FIG. 1 shows schematically the configuration of a variable frequency or tunable Fabry Perot interferometer 1 wherein two mirrors (2, 3) are fixed parallel to each other by a spacer 4. The spacer 4 is connected to a drive unit 5 and makes possible a change of the distance (x) of the mirrors (2, 3) to each other. The mirrors (2, 3) comprise substrates (6, 7) which are provided on the surface with reflecting coatings (8, 9). The transmission characteristics of the coatings (8, 9) are configured in such a manner that predetermined spectral ranges can be evaluated. The spectral ranges ($\Delta\lambda_1$, $\Delta\lambda_2$), which can be evaluated, cover the wavelengths between 3.5 micrometers and 4.5 micrometers and 8 micrometers to 12 micrometers.

It is assumed that a measurement beam 10 is directed perpendicularly to the surface of the upper mirror 2. The transmissions of the mirrors (2, 3) result in dependence upon the mirror spacing (x). The drive unit 5 is so adjusted that a mismatch of the transmissions within the pregiven spectral ranges is possible. In the following, the interferometer 1 which corresponds to FIG. 1 is a double band Fabry Perot interferometer and is referred to as a DB-FP interferometer.

Figure 2:
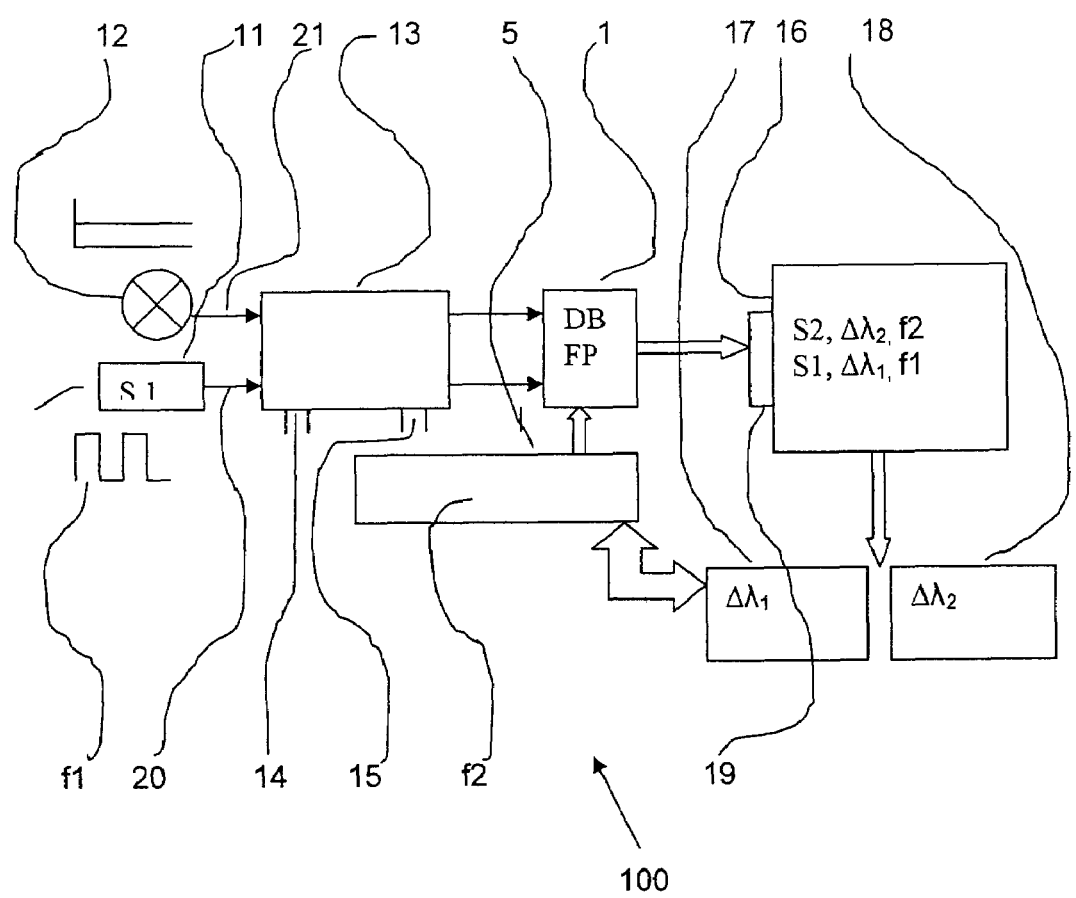
FIG. 2 shows a first gas concentration measuring apparatus having two radiation sources; and, FIG. 3 shows a second gas concentration measuring apparatus having a single radiation source.

FIG. 2 shows schematically a first gas measuring apparatus 100 which includes the DB-FP interferometer 1 of FIG. 1.

The first gas measuring apparatus 100 comprises a first radiation source 11, a second radiation source 12, a downstream connected measuring gas cuvette 13 for the gas sample to be investigated having a gas inlet 14 and a gas outlet 15; the DB-FP interferometer 1 having the drive unit 5; a double band detector 19; an evaluation unit 16 for separating the measurement signals ($S_1$, $S_2$) assigned to the spectral ranges ($\Delta\lambda_1$, $\Delta\lambda_2$); and, signal outputs (17, 18) for the measurement signals ($S_1$, $S_2$) assigned to the spectral ranges ($\Delta\lambda_1$, $\Delta\lambda_2$). The components in FIG. 2, which are the same as in FIG. 1, have the same reference numerals.

The first radiation source 11 is configured as a radiation source which can be rapidly modulated and emits up to a wavelength of approximately 6 micrometers. The wavelength range between 3.5 micrometers and 4.5 micrometers is covered by the first radiation source 11. The first radiation source 11 preferably comprises a thin, coiled tungsten filament having a thickness of 6 micrometers to 8 micrometers. The modulation frequency $f_1$ lies in a range between 11 Hertz and 25 Hertz. The second radiation source 12 is driven in DC voltage operation and is a broadband radiator which covers the wavelength range of 8 micrometers to 12 micrometers.

The measuring beams (20, 21), which are emitted by the radiation sources (11, 12), reach the two-band detector 19 via the measuring gas cuvette 13 and the DB-FP interferometer 1. The tuning of the DB-FP interferometer 1 takes place at the frequency $f_2$. The measuring signal, which is supplied by the two-band detector 19, comprises a superposition of the measuring beams (20, 21) which are supplied by the radiation sources (11, 12). The evaluation unit 16 operates in accordance with the lock-in principles. In the evaluation unit 16, the measuring signals ($S_1$, $S_2$) are so processed while utilizing the frequencies $f_1$ and $f_2$ that they can be assigned to the spectral ranges ($\Delta\lambda_1$, $\Delta\lambda_2$) and are available at the signal outputs (17, 18) as measuring signals $S_1$ and $S_2$.

Figure 3:
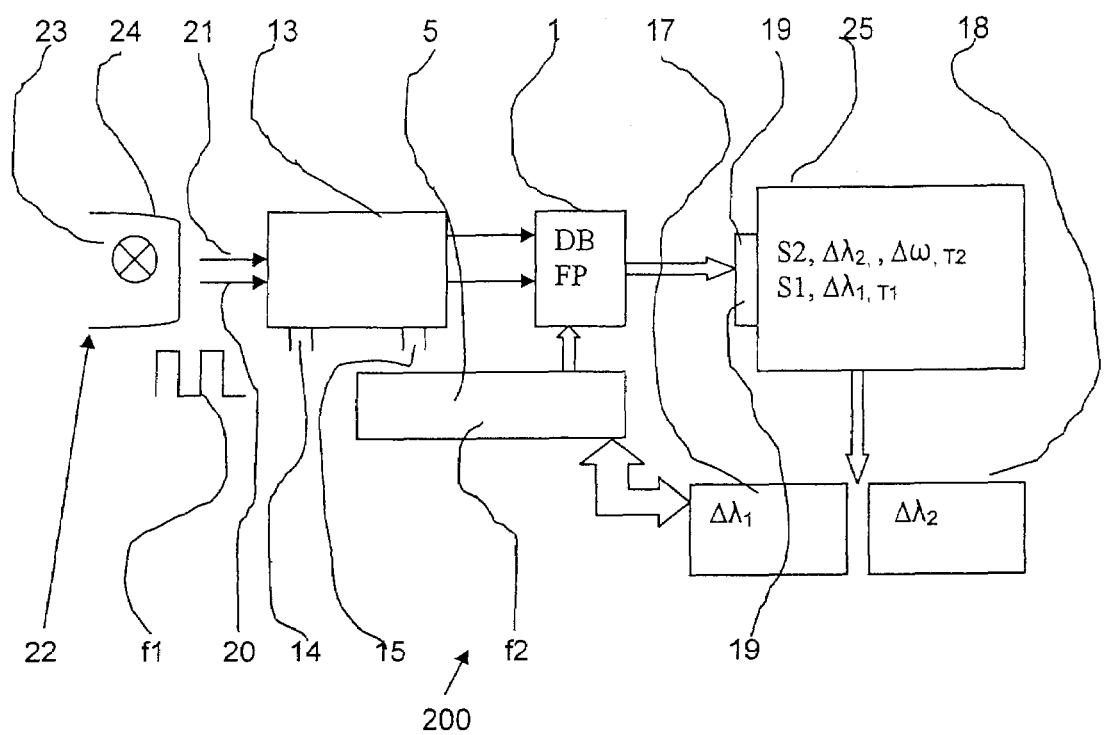

FIG. 3 shows a second gas measuring apparatus 200 wherein the radiation sources (11, 12) of the first gas measuring apparatus 100 of FIG. 1 are replaced by a single radiation source 22. The components of FIG. 3, which are the same as in FIGS. 1 and 2, are provided with the same reference numerals.

The single radiation source 22 comprises a thin, coiled tungsten filament 23 having a thickness between approximately 6 micrometers and 8 micrometers and is driven at a modulated voltage of the frequency $f_1$. The tungsten filament 23 is accommodated in a quartz glass envelope 24 which functions as a passive emitter. The quartz glass envelope 24 is so dimensioned that it makes possible a transmission of the emitted radiation of the tungsten filament 23 up to approximately 6 micrometers. In this way, and with the tungsten filament 23, the spectral range having the wavelengths between 3.5 micrometers and 4.5 micrometers is covered. The quartz glass envelope 24 is heated by the tungsten filament 23 and is doped in such a manner that it preferably emits in the spectral range between 8 micrometers and 12 micrometers. The quartz glass envelope 24 emits the radiation likewise at the frequency $f_1$ of the tungsten filament 23, however, at a phase shift of $\Delta\omega$ relative to the tungsten filament 23. The phase shift $\Delta\omega$ is used to separate the measuring signals ($S_1$, $S_2$) in an evaluation unit 25 connected downstream of the two-band radiation detector 19. Alternatively or in addition, the radiation temperatures ($T_1$, $T_2$), which result from the Planck equation and are assigned to the spectral ranges, can be used to detect the spectral ranges.

It is understood that the foregoing description is that of the preferred embodiments of the invention and that various changes and modifications may be made thereto without departing from the spirit and scope of the invention as defined in the appended claims.

What is claimed is:

1. A gas measuring apparatus for measuring a gas sample of inhalation anesthetics, carbon dioxide and nitrous oxide, the apparatus comprising:

a radiation source for emitting radiation in first and second spectral ranges ($\Delta\lambda_1$, $\Delta\lambda_2$);

said radiation source being a component comprising: a radiator which is modulated at a frequency ($f_1$); and, a quartz glass envelope defining a broadband radiator and being mounted over said radiator;

a measuring gas cuvette for accommodating the gas sample to be examined;

a mirror assembly including: first and second reflecting mirrors disposed at a distance from each other; and, means for changing said distance between said mirrors;

said mirror assembly being configured on the basis of an electrically tunable Fabry Perot interferometer which provides transmissions corresponding to said first and second spectral ranges ($\Delta\lambda_1$, $\Delta\lambda_2$);

a detector element for evaluating said first and second spectral ranges ($\Delta\lambda_1$, $\Delta\lambda_2$);

a drive unit connected to said mirror assembly for presetting a dynamic range with a frequency ($f_2$) for changing said distance so as to permit a first spectral range ($\Delta\lambda_1$) to be detected in a transmission range of between approximately 3.5 micrometers and 4.5 micrometers and a second spectral range ($\Delta\lambda_2$) to be detected in a transmission range of between approximately 8 micrometers and 12 micrometers;

measuring signals ($S_1$, $S_2$) being assigned to said spectral ranges ($\Delta\lambda_1$, $\Delta\lambda_2$), respectively; and, an evaluation unit for separating said measuring signals ($S_1$, $S_2$) assigned to said spectral ranges ($\Delta\lambda_1$, $\Delta\lambda_2$).

2. The gas measuring apparatus of claim 1, wherein said frequencies ($f_1$, $f_2$) and a phase shift ($\Delta\omega$) between said modulated radiator and said broadband radiator are parameters for separating said measuring signals ($S_1$, $S_2$).

3. The gas measuring apparatus of claim 1, wherein said evaluation unit operates according to the lock-in principle.

4. A gas measuring apparatus for measuring a gas sample of inhalation anesthetics, carbon dioxide and nitrous oxide, the apparatus comprising:

a radiation source for emitting radiation in first and second spectral ranges ($\Delta\lambda_1$, $\Delta\lambda_2$);

said radiation source comprising a first radiation source modulated at a frequency ($f_1$) and having an emission range below 6 micrometers; and, a second radiation source configured as a broadband radiator;

a measuring gas cuvette for accommodating the gas sample to be examined;

a mirror assembly including: first and second reflecting mirrors disposed at a distance from each other; and, means for changing said distance between said mirrors;

said mirror assembly being configured on the basis of an electrically tunable Fabry Perot interferometer which provides transmissions corresponding to said first and second spectral ranges ($\Delta\lambda_1$, $\Delta\lambda_2$);

a detector element for evaluating said first and second spectral ranges ($\Delta\lambda_1$, $\Delta\lambda_2$);

a drive unit connected to said mirror assembly for presetting a dynamic range with a frequency ($f_2$) for changing said distance so as to permit a first spectral range ($\Delta\lambda_1$) to be detected in a transmission range of between approximately 3.5 micrometers and 4.5 micrometers and a second spectral range ($\Delta\lambda_2$) to be detected in a transmission range of between approximately 8 micrometers and 12 micrometers;

measuring signals ($S_1$, $S_2$) being assigned to said spectral ranges ($\Delta\lambda_1$, $\Delta\lambda_2$), respectively; and, an evaluation unit for separating said measuring signals ($S_1$, $S_2$) assigned to said spectral ranges ($\Delta\lambda_1$, $\Delta\lambda_2$).

5. The gas measuring apparatus of claim 4, wherein said frequencies ($f_1$, $f_2$) and a phase shift ($\Delta\omega$) between said modulated radiator and said broadband radiator are parameters for separating said measuring signals ($S_1$, $S_2$).

6. The gas measuring apparatus of claim 4, wherein said evaluation unit operates according to the lock-in principle.

\* \* \* \* \*